United States Patent
Tekautz et al.

(10) Patent No.: US 10,316,011 B2
(45) Date of Patent: Jun. 11, 2019

(54) PROCESS FOR THE PRODUCTION OF 2, 5-FURANDICARBOXYLIC ACID (FDCA)

(71) Applicants: ANNIKKI GMBH, Raaba-Grambach (AT); MICROINNOVA ENGINEERING GMBH, Allerheiligen b. Wildon (AT)

(72) Inventors: Gunter Tekautz, Graz (AT); Dirk Kirschneck, Albersdorf-Prebuch (AT); Walter Linhart, Graz (AT)

(73) Assignees: ANNIKKI GMBH, Raaba-Grambach (AT); NOVOLANA GMBH, Tobelbad (AT)

( * ) Notice: Subject to any disclaimer, the term of this patent is extended or adjusted under 35 U.S.C. 154(b) by 0 days.

(21) Appl. No.: 16/060,382

(22) PCT Filed: Dec. 7, 2016

(86) PCT No.: PCT/EP2016/080107
§ 371 (c)(1),
(2) Date: Jun. 7, 2018

(87) PCT Pub. No.: WO2017/097843
PCT Pub. Date: Jun. 15, 2017

(65) Prior Publication Data
US 2018/0362486 A1    Dec. 20, 2018

(30) Foreign Application Priority Data
Dec. 10, 2015  (EP) .................................... 15199377

(51) Int. Cl.
C07D 307/68  (2006.01)
(52) U.S. Cl.
CPC ................. C07D 307/68 (2013.01)
(58) Field of Classification Search
CPC .................................................. C07D 307/68
USPC ....................................................... 549/485
See application file for complete search history.

(56) References Cited

U.S. PATENT DOCUMENTS 8,193,382 B2 *  6/2012  Lilga .................... C07D 307/48
549/489

FOREIGN PATENT DOCUMENTS

| JP | 2009-013079 A | 1/2009 |
| WO | 2012161967 A1 | 11/2012 |
| WO | 2014122319 A1 | 8/2014 |

OTHER PUBLICATIONS

International Search Report cited in PCT/EP2016/080107, dated Jan. 30, 2017 (4 Pages).
Marcel L. Ribeiro et al: "Cooperative effect of colbat acetylacetonate and silica in the catalytic cyclization and oxidation of fructose to 2,5-furandicarboxylic acid", Catalysis Communication, vol. 4, No. 2, Feb. 1, 2003 (Feb. 1, 2003), pp. 83-86.

* cited by examiner

*Primary Examiner* — Niloofar Rahmani
(74) *Attorney, Agent, or Firm* — Workman Nydegger

(57) ABSTRACT

The present invention relates to a process for the production of 2,5-furandicarboxylic acid (FDCA) via oxidation of 5-hydroxymethyl-2-furfural (HMF), said HMF being present in a solution in a high-boiling polar solvent and water. The process is characterized by the combination of —a first oxidation step wherein the HMF is at least partly oxidized in said solution to yield a first reaction mixture comprising at least one monoacid selected from the group consisting of -hydroxymethylfuran-2-carboxylic acid (HMFA), 5-formylfuran-2-carboxylic acid (FFCA) and, optionally, FDCA —an extraction step after the first oxidation step wherein said high-boiling polar solvent is extracted from said first reaction mixture by means of an extraction solvent, wherein said at least one monoacid remains in an aqueous phase, —a second oxidation step wherein said at least one monoacid is oxidized to FDCA.

12 Claims, 2 Drawing Sheets

PROCESS FOR THE PRODUCTION OF 2, 5-FURANDICARBOXYLIC ACID (FDCA)

FIELD OF THE INVENTION

The present invention relates to a process of oxidizing 5-Hydroxymethylfurfural available in a solvent or solvent mixture containing at least one high boiling, polar solvent (hbS) producing 2,5-furandicarboxylic acid.

STATE OF THE ART 2,5-furandicarboxylic acid (hereinafter referred to as FDCA) is accessible from renewable resources and it is an interesting intermediate for molecules in various applications like agricultural chemicals, drugs, pesticides, pharmacology or antibacterial agents. The most important group of FDCA conversions is the polymeristion to polyamides, polyesters or polyhydrazines. (Lewkowski, 2001)

Catalytic oxidation of 5-hydroxymethylfurfural (hereinafter referred to as HMF) derived from dehydration of hexoses is potentially the most important way to synthesize FDCA from renewable resources. A lot of different approaches for the oxidation of HMF yielding FDCA as main product are known in the literature. But there is no process described making an easy coupling of HMF formation and oxidation possible. This is mainly due to different types of solvents used for these steps.

The HMF oxidation to FDCA, in the first step, runs over diformylfuran (hereinafter referred to as DFF) or hydroxymethylfurancarboxylic acid (HMFCA) and in the following step over formylfurancarboxylic acid (FFCA). The principal scheme is shown below:

U.S. Pat. No. 8,865,921 describes a Co/Mn/Br catalytic system, which is also used for terephthalic acid synthesis, for oxidation of HMF, but also of HMF esters, 5-(chloromethyl)furfural and other related compounds. These processes are also carried out in acetic acid or mixtures of acetic acid with water. The same chemical system and solvents with different technical approaches are described in U.S. Pat. No. 8,242,292, which describes an improvement by continuous removal of water, and WO 2013/033058), in which the reaction is carried out in a spray reactor. Both processes run in acetic acid or acetic acid/water mixtures.

Oxidation of HMF in aprotic media has been described only for the purpose of selective oxidation to diformylfuran. U.S. Pat. No. 7,700,788 describes the oxidation of HMF to DFF in methylene chloride.

The starting material for the oxidation step at issue here, HMF, is an important intermediate achieved from dehydration of hexoses (glucose, fructose). This synthesis in opposite to the oxidation is usually not carried out in water due to low yields. Maximum HMF yields achieved in water lie in the range between 50% and 60%.

Tuercke et al. (2009) describe a continuous, HCl catalyzed microreactor process in water yielding 54% HMF.

High selectivities for the dehydration of fructose or glucose are achieved only in high boiling, polar, aprotic solvents such as Dimethylsulfoxide (DMSO), N-Methyl-2-pyrrolidon (NMP), N,N-Dimethylformamide (DMF) or N,N-Dimethylacetamide (DMA).

Nowadays, mainly DMSO is used as a solvent, as described in U.S. Pat. No. 4,590,283 (Roquette Freres). But also DMF, DMA or NMP show high selectivities and excellent yields, as described in the same document or in more recent ones like EP 2 703 395 or U.S. Pat. No. 7,317,116 B2.

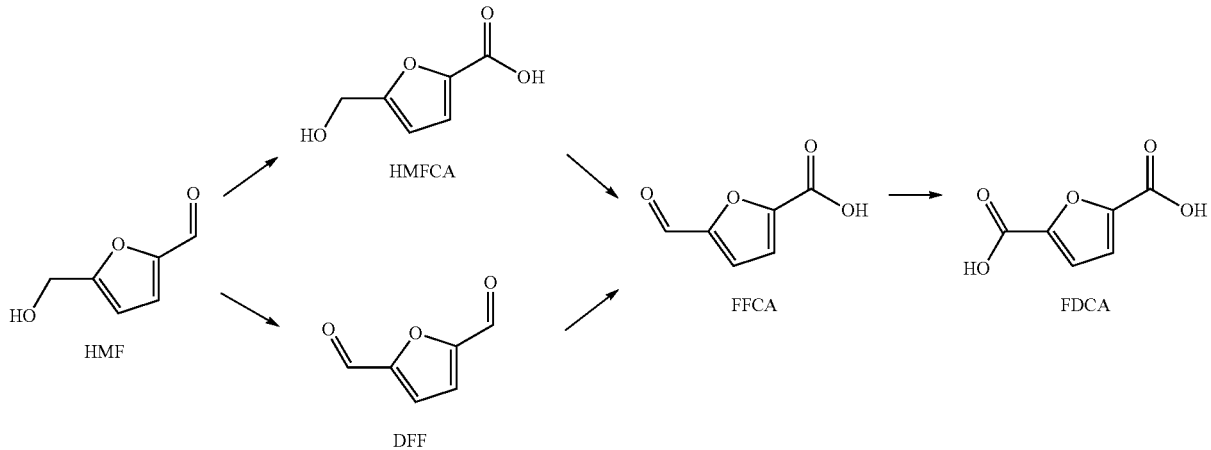

Most commonly the oxidation is carried out in water, alcohols or carboxylic acids. U.S. Pat. No. 3,326,944 describes the oxidation of HMF to FDCA in water with sodium hydroxide and platinum type catalysts (hereinafter referred to as PTC).

EP 0 356 703 describes the oxidation of HMF in an aqueous environment with PTC and at pH value of maximum 8. This value is controlled during the process by continuous addition of base.

In U.S. Pat. No. 8,193,382 the same oxidation in water or acetic acid is documented. Weak bases like carbonates or phosphates are used as bases in this case. Catalysts used for this process are also PTC.

For these processes, in order to go into the oxidation step, removal of the high boiling solvent or at least a significant amount thereof is necessary.

Another approach employs water as solvent and biphasic systems to extract HMF to the organic phase in order to avoid rehydration. Such approaches show excellent results up to 90% HMF yield. Still, however, in order to achieve such good results, an addition of DMSO or NMP to the water phase is necessary. This solvent is then also extracted to the organic phase and needs to be separated from the HMF, making the process economically unfavored. The improvements of this approach only lies in the smaller amount of high boiling solvent that needs to be removed. See (Chheda et al., 2007).

A review of the scientific literature to HMF formation from hexoses separated to aqueous media and polar aprotic solvents is given by (Teong et al., 2014).

PCT-application PCT/EP2015/063578 (not pre-published) discloses the selective production of oxidized furan derivatives starting from HMF wherein the oxidation process is carried out continuously in flow, there are provided means for varying reaction parameters, the solvent for the oxidation process is water and a dipolar aprotic solvent. Especially NMP is present as a co-solvent.

At the actual state of the art the step of HMF oxidation has to be done in a different solvent as the previous HMF formation if both steps should reach high yields. Usually HMF is isolated after dehydration before being forwarded to the oxidation step, which needs high effort to separate the high boiling solvent and leads to a decrease of the HMF yield.

Solvent removal can be accomplished by evaporation. However, it was found that in doing so it is necessary to keep temperatures below 50° C. to avoid decomposition of HMF. Accordingly very low pressures are necessary to be able to remove the high boiling solvents. This is nearly impossible and very expensive to be done for large scale industrial processes.

An alternative approach is the extraction of the high boiling solvent. However, the solubility of HMF in organic solvents capable to extract polar, high boiling solvents is good and, thus, large amounts of HMF are lost to the organic phase.

To avoid obvious problems with separation of HMF from high boiling polar solvents, several different approaches were taken.

Bicker (Bicker et al., 2005) described dehydration in supercritical fluids like different acetone/water mixtures, achieving full conversion and yields of 77%.

EP 1 427 715 B2 describes a one pot synthesis of DFF from a carbohydrate. In the first step the dehydration to HMF is done and in the second the oxidation to DFF with vanadium compounds as catalyst.

Also the oxidation of HMF to DFF in DMSO can be found in the literature, as described by Grasset et al. (2013), using intercalated vanadium phosphate oxides as catalyst, or by Amarasekara et al. (2008), using Mn(III)-salen catalysts. An oxidation of HMF to FDCA in these systems is not described.

It would be advantageous to go directly from the dehydration step to the oxidation step without additional work-up in order to achieve an economical process.

Ribeiro et al (2003) have proposed a one pot reaction in labscale from fructose to FDCA with cobalt acetylacetonate in a sol-gel silica as catalyst. They achieved excellent yield of 72% over both steps. Still, the viability of this reaction system for large scales is questionable.

To the present inventor's best knowledge, up to now no technical feasible method was described to combine the synthesis of HMF with a subsequent oxidation of HMF without costly work-up in between.

This problem is solved by the process according to claim 1. Advantageous embodiments of the present invention are disclosed in the sub-claims.

DETAILED DESCRIPTION OF THE INVENTION

Figure 1:
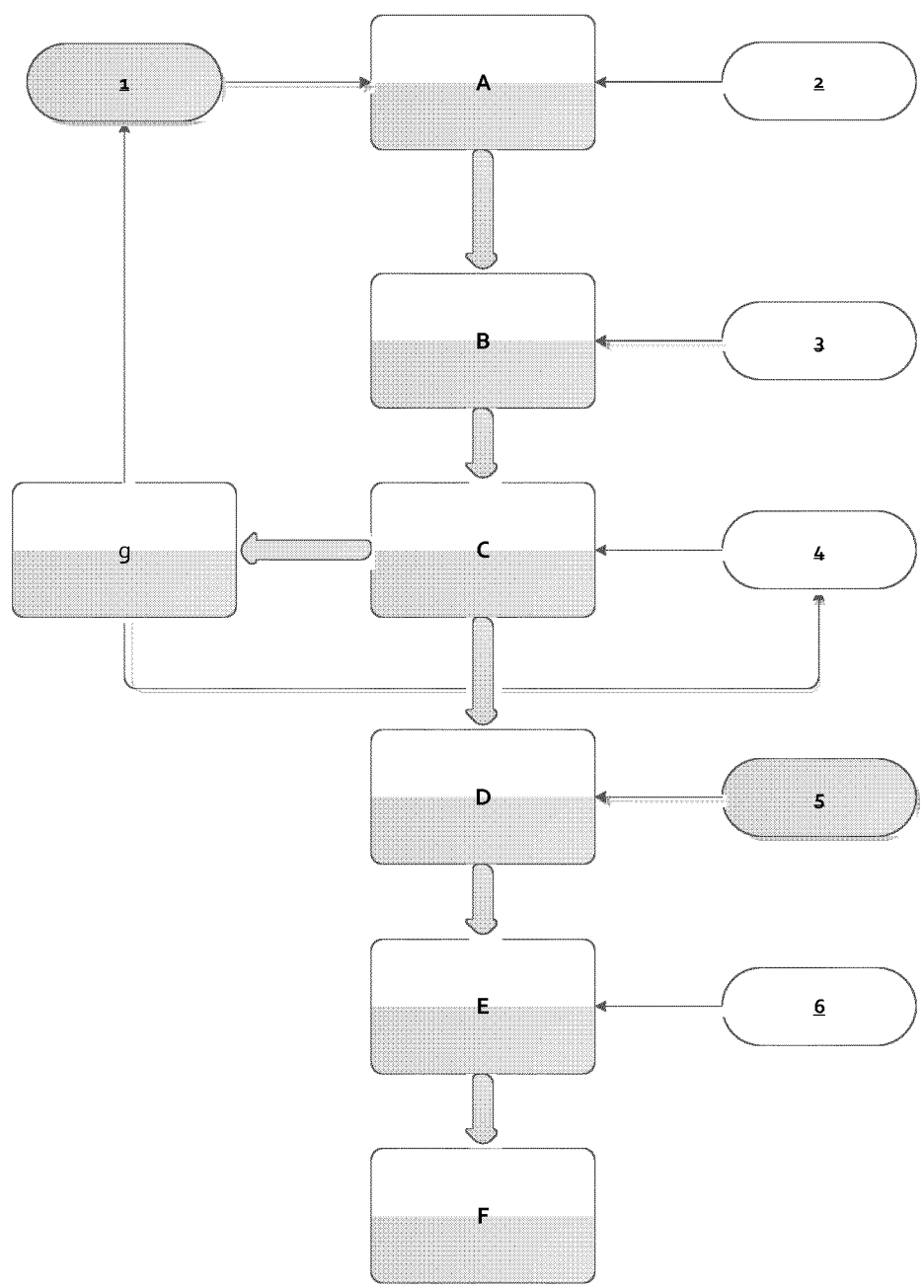
FIG. 1 is a process diagram exemplifying a preferred embodiment of the present invention.

Surprisingly, the present inventors have found an improved economical process that enables to oxidize HMF in high boiling, polar solvents to FDCA without the need to isolate or concentrate HMF before the oxidation step.

Accordingly, in one aspect the present invention relates to a process for the production of 2,5-furandicarboxylic acid (FDCA) via oxidation of 5-hydroxymethyl-2-furfural (HMF), said HMF being present in a solution in a high-boiling polar solvent and water, wherein said process is characterized by the combination of a first oxidation step wherein the HMF is at least partly oxidized in said solution to yield a first reaction mixture comprising at least one monoacid selected from the group consisting of 5-hydroxymethylfuran-2-carboxylic acid (HMFA) and 5-formylfuran-2-carboxylic acid (FFCA) and, optionally, FDCA an extraction step after the first oxidation step wherein said high-boiling polar solvent is extracted from said first reaction mixture by means of an extraction solvent, wherein said at least one monoacid remains in an aqueous phase, a second oxidation step wherein said at least one monoacid is oxidized to FDCA.

For the purposes of the present invention, a "high-boiling polar solvent" (in the following also abbreviated as "hbs") means a solvent that has a boiling point higher than water and is miscible with water.

Preferably, the high-boiling polar solvent is selected from the group consisting of polar aprotic solvents and mixtures thereof. The skilled artisan understands that solvents having a permittivity of 5 or more, in particular 15 or more, are considered to be polar and that solvents containing no hydrogen atoms that can be donated into an hydrogen bond are considered to be aprotic. Especially preferred are apolar aprotic solvents all hydrogen atoms of which (if any) are covalently bound to a carbon atom.

More preferably, the high-boiling polar solvent is selected from the group consisting of Dimethylsulfoxide (DMSO), N-Methyl-2-pyrrolidone (NMP), N,N-Dimethylformamide (DMF) or N,N-Dimethylacetamide (DMA) and mixtures thereof. The most preferred solvent is NMP.

It has surprisingly been found that it is possible to carry out oxidation of HMF to FDCA without the need of prior removal of the high boiling polar solvent of a preceding step to obtain HMF by a three-step process:

In the first step, HMF is oxidized in a mixture of high boiling polar solvent and water as completely as possible to at least one of the monoacid oxidation products of HMF (FFCA, HMFCA) and, eventually, also already in part FDCA. Especially, in the first step a mixture of FFCA, HMFCA and FDCA may be obtained.

The second step is the extraction of the high boiling polar solvent from an alkaline solution leaving the salts of the monoacids and the FDCA completely in the aqueous phase. Any unreacted HMF from the first step as well as DFF as by-product of the first step are transferred into the organic phase of this extraction.

In the third step, the oxidation of the monoacids to FDCA is completed in water. All three steps can be done in a batchwise operation as well as in a continuous one.

For the first oxidation step, a partial oxidation of HMF is performed at mild conditions. High pressures, high temperatures, high basicity or high base concentrations can be avoided as no complete conversion to FDCA is targeted. The conditions in this step are selected to avoid DFF formation and maximize formation of monoacids and FDCA.

Especially, it has been found that while it would be principally possible to oxidize the HMF to FDCA in one step by employing strong bases, certain amounts of HMF are degraded during the reaction, resulting in solid impurities that may block the reactor, thus making this option unsuitable especially in the case of a continuous reaction design.

Thus, it has been found to be advantageous to employ weak bases, such as with a pKa value of from 7.5 to 13 in the first oxidation step. The base is preferably selected from the group consisting of carbonates and phosphates, especially anorganic carbonates and phosphates. Most preferably, $Na_3PO_4$ and/or $Na_2HPO_4$ is employed as a base.

The pH value for the first oxidation step may in particular be between 10 and 12. The molar amount of the base employed may be at least twice the molar amount of HMF to ensure deprotonation of the acid group.

Thus, the conditions are selected such that the acidic groups formed in the oxidation step are transferred into salt form as completely as possible, only the salt from being soluble in the aqueous solution.

Furthermore, the usage of certain amounts of water has been found to be advantageous.

If no water is already present in the reaction mixture of a preceding HMF production, it has to be added for this oxidation step. This simply can be done together with the base addition. The water content in the solution may range between 1 and 80%. More preferable is a water content of 40 to 60%.

Further preferred conditions for the first oxidation step are:
  the oxidant is air or oxygen
  the molar excess of oxygen to HMF is 0.5 to 1.5 times, preferably 0.9 to 1.4 times, most preferred 1.25 times
  the reaction pressure is in a range of 1 bar to 100 bar, preferably 5 bar to 40 bar, most preferred 20 bar
  the temperature is in a range of from 50° C. to 130° C., preferably 60° C. to 100° C., most preferred 90° C.
  the residence time during the reaction is 30 minutes or less, preferably 15 minutes or less Only part of the above parameters may be set as detailed above. Preferably, a combination of several or, most preferably, all of the above conditions may be applied.

The catalyst to be used for the first oxidation step may be any suitable oxidation catalyst, such as platinum type catalysts (PTC), CuO/AgO, CuO or CoO. Preferably a mixed copper oxide/silver oxide catalyst is used.

The reaction medium (RM1) obtained in the first oxidation step contains mainly HMFCA, FFCA and FDCA.

In the second step the high boiling polar solvent is extracted with a suitable low boiling organic solvent (Extraction). Unreacted HMF and DFF go into the organic phase, whereas the salts of the monoacids (HMFCA, FFCA) and the target product FDCA remain in the water phase.

The extraction solvent for the extraction step is preferably a low boiling solvent, and more preferably is selected from ethylacetate, trichloromethane and mixtures thereof. These solvents showed excellent results with regard to necessary solvent amount and number of extraction steps in the extraction of the high boiling polar solvent from the reaction mixture. A batchwise as well as a continuous extraction is viable.

The aqueous phase obtained in the extraction step is subjected to a second oxidation step in order to complete the oxidation to FDCA. The second oxidation step can be carried out employing more harsh conditions as compared with the first oxidation step in order to complete the oxidation of the monoacids. HMF and DFF, being the most unstable compounds in the process, are no longer available in the reaction mixture at this stage. Additionally, the presence of water as a solvent at this stage avoids problems of possible spontaneous solvent oxidation at high concentrations of the oxidizing agent and safety issues connected therewith. Furthermore, possible deprotonation initiated decomposition reactions of the high boiling polar solvent with strong bases, leading to precipitates and a loss of expensive solvent, can be avoided this way.

Thus, for the second oxidation step, any base can be used to keep the pH value in a basic regime of between 7.0 to 14.0, and more preferable between 10.0 and 12.0. More preferably, sodium or potassium hydroxide are used.

Further preferred conditions for the second oxidation step are:
  the oxidant is air or oxygen
  the molar excess of oxygen to HMF is 0.5 to 5 times preferably 1.0 to 3.0 times, most preferred 2.0 times
  the reaction pressure is in a range of 1 bar to 100 bar, preferably 5 bar to 40 bar, most preferred 20 bar
  the temperature is in a range of from 80° C. to 180° C., preferably 90° C. to 130° C., most preferred 110° C.
  a base with a pKa value of above 13, most preferably NaOH, is employed
  the residence time during the reaction is 30 minutes or less, preferably 15 minutes or less Again, only part of the above parameters may be set as detailed above. Preferably, a combination of several or, most preferably, all of the above conditions is applied.

The catalyst for the second oxidation step, again, may be any suitable oxidation catalyst. Preferably, platinum based catalysts are employed.

The FDCA obtained in the second oxidation step may be converted to the free acid by means of an aqueous acid. The free acid precipitating from the reaction mixture may be isolated by means of filtration.

As mentioned above, according to a preferred embodiment of the present invention, in said first oxidation step parts of the HMF remain unreacted and/or are oxidized to 2,5-diformylfuran (DFF) and in said extraction step said unreacted HMF and/or said DFF are extracted from said first reaction mixture.

Said extracted unreacted HMF and/or said extracted DFF are preferably recycled to the solution before the first oxidation step.

A further preferred embodiment of the present invention is characterized in that, after the extraction step, the extraction solvent and the high boiling polar solvent are separated from each other.

Especially, both extraction solvent and high boiling solvent may be recycled. The recycling ratio may be in a range of from 40 to 99%.

The separation may be carried out by distilling off the low boiling extraction solvent. The extraction solvent can be recycled into the extraction step.

The high boiling polar solvent may be recycled to a preceding HMF synthesis step. Especially in case the high boiling polar solvent contains significant amounts of unreacted HMF and/or DFF after the extraction step, the high boiling polar solvent may also be recycled to the first oxidation step. Before being recycled, the high boiling polar solvent may be purified. Any water immiscible organic solvent can be used to extract the high boiling polar solvents at this stage.

The process of the present invention may be carried out batchwise or in a continuous fashion. The process of the present invention is especially advantageous in the context of a continuous process design. In this regard, the process of the present invention can advantageously be combined with a preceding process for obtaining HMF, especially if also this preceding step is carried out in a continuous fashion.

FIG. 1 shows a process diagram exemplifying a preferred embodiment of the present invention:

A mixture of fructose and high-boiling solvent (1) and a mixture of HCl and water (2) are fed to a dehydration step (A). In the dehydration step (A), HMF in a mixture of water and high-boiling solvent is obtained.

This mixture is subjected to a first oxidation step (B), employing an aqueous base, and air or oxygen as oxidation agent (3).

The mixture obtained from the first oxidation (B), containing HMFCA and/or FFCA and, optionally FDCA, as well as residual HMF and DFF, is subjected to an extraction step (C) employing an extraction solvent 4.

The organic phase obtained after extraction, containing the HMF, DFF, the high-boiling solvent as well as the extraction solvent may be subjected to a distillation step (g). High boiling solvent, optionally containing HMF and DFF, is recycled to the starting solution (1) in large part.

The extraction solvent is recycled to the extraction step (4).

The water phase containing HMFCA and/or FFCA and, optionally, FDCA is subjected to the second oxidation (D) step utilizing an aqueous solution of a strong base and air or oxygen as oxidizing agent (5).

Upon completion of the oxidation, the reaction mixture is neutralized or acidified (E) with an aqueous acid (6) to convert the FDCA salt into free acid, which precipitates from the aqueous phase.

In a filtration step (F) solid FDCA is obtained from the reaction mixture.

EXAMPLES

1.) NMP/NaOH/Pt—C/Air/22 Bar/90° C.

i) Oxidation 1—in NMP, Pt—C, 17 Bar and 80° C., NaOH

The starting solution A is prepared by dissolving 5-Hydroxymethylfurfural (99%) in 95 g NMP (99.5%, Sigma Aldrich) and 5 g deionized water. The starting solution B is a 15% NaOH solution, prepared from 150.41 g NaOH and 850.18 g deionized water.

In a continuous flow plant, solution A and solution B are contacted in a 1/16" t-piece. The flow rate for solution A is 0.08 ml/min, and for solution B 0.06 ml/min. The mixture obtained is directly contacted with 125 ml/min air flow, before the mixture enters the actual reactor. In this case the reactor was a trickle bed reactor using platinum on activated carbon as catalyst. The double jacketed reactor is heated to 80° C. and provides a residence time of 30 minutes for the given flow rates. The whole system is pressurized to 22 bar with a pressure maintaining valve.

The reaction mixture obtained in this step contains no HMF. The oxidation product mixture contains, according to HPLC analysis, FDCA: 73.67%, HMFCA: 18.10%, FFCA: 7.67%, DFF: 0.41% and 0.15% unknown oxidation products. Additionally, a small amount of dark, solid material is yielded using this procedure, leading to a reduced lifetime cycle of the catalyst fixed bed.

ii.) Extraction with Ethyl Acetate

The reaction mixture (20.4 ml) collected from the first oxidation step was extracted six times using 20 ml ethyl acetate per cycle to remove NMP. The HPLC chromatogram showed no loss of the acids in the aqueous phase after this procedure. The DFF was transferred completely to the organic phase.

iii.) Oxidation 2—in $H_2O$, Pt—C, 17 Bar and 80° C., NaOH

The aqueous solution of the acids (FCDA, HMFCA and FFCA) obtained from the extraction is pumped with a flow rate of 0.08 ml/min into a t-piece mixer to be mixed with a stream of 0.06 ml/min 15% caustic solution in a t-piece mixer. This basic mixture is contacted with air in a t-piece. (flow rate air is 125 min/min). This mixture is led into the trickle bed reactor filled with platinum on activated charcoal as catalyst. The hold up time in the reactor is 30 minutes at 100° C. The whole plant setup is kept at a pressure of 25 bar. Sampling was done continuously at room temperature. The reaction mixture obtained contained 100.0% FDCA according to the HPLC spectra. The yield of the overall process according to quantitative HPLC analytics was 82%.

2.) $DMSO/Na_2HPO_4$/Pt—C/Air/17 Bar/80° C.

i) Oxidation 1—in DMSO, Pt—C, 17 Bar and 80° C., $Na_2HPO_4$

The process was carried out in an equivalent continuous lab-plant setup as in example 1. Starting solution A was prepared by mixing 32.8 g HMF and 200.3 g DMSO; solution B was a 11.5% solution of disodium hydrogenphosphate prepared by making a saturated mixture (38.15 g $Na_2HPO_4$ and 45 g of deionized water) diluted with deionized water twice in volumetric ratio of 1:1.

The processing parameters were 30 minutes residence time at 80° C. and 18 bar. The catalyst used was platinum on activated carbon.

The oxidation product mixture contains, according to HPLC analysis, FDCA: 9.33%, HMFCA: 4.11%, FFCA: 27.67%, DFF: 16.23% and 41.70% of HMF. About 1% are unidentified side products.

ii.) Extraction with Trichloromethane

DMSO extraction was carried out with trichloromethane. 21.1 ml reaction mixture was extracted six times with 20 ml trichloromethane in each cycle.

DFF was extracted completely to the organic phase. The acids remained completely in the water phase, as well as some unreacted HMF (4.7% according to HPLC).

iii.) Oxidation 2—in $H_2O$, Pt—C, 17 Bar and 80° C., NaOH

The water phase from the extraction step was processed in a second oxidation step. The flow rates in this step were 0.08 for the reaction mixture from the extraction, 0.06 for the aqueous 11.5% $Na_2HPO_4$ solution and 125 mln/min air. The catalyst used was platinum on activated carbon, and the processing parameters were 100° C. and 22 bar.

The achieve reaction mixtures contained 57.80% FDCA, 13.64% HMFCA and 23.14% FFCA. The yield for the overall process was determined by quantitative HPLC to be 37%.

3.) NMP/$Na_2HPO_4$/CuO/$Al_2O_3$/Air/17 Bar/80° C.

i) Oxidation 1—in NMP, Pt—C, 17 Bar and 80° C., $Na_2HPO_4$

The process was carried out in a comparable, scaled up continuous lab-plant setup as used in the examples above. Starting solution A was prepared by mixing 65.6 g HMF and 400.0 g NMP; solution B was a 15% solution of sodium phosphate, prepared by mixing 150.0 g $Na_2HPO_4$ and 850.0 g of deionized water.

The flow rates used in this trial were 2.86 ml/min solution A, 2.14 ml/min solution B and 250.0 nml/min for air. Further processing parameters were 10 minutes residence time at 90° C. and 18 bar. The catalyst used was copper oxide on aluminium oxide.

The oxidation product mixture obtained from this trial contains, according to HPLC analysis, FDCA: 9.20%, HMFCA: 86.39%, FFCA: 0.13%, DFF: 0.36% and 2.82% of HMF. About 1% are unidentified side products.

ii.) Extraction with Ethyl Acetate

NMP extraction was carried out with ethylacetate. 50 ml reaction mixture was extracted six times with 40 ml ethyl acetate in each cycle.

FDCA, HMFCA and FFCA remained completely in the water phase. Also a small amount of HMF was found in the water phase (0.5% according to HPLC). DFF completely went into the organic phase and was discarded.

iii.) Oxidation 2—in $H_2O$, Pt—C, 17 Bar and 90° C., NaOH

The water phase from the extraction step was processed in a second oxidation step in the smaller lab scale setup used also in example 1 and 2. Flow rates in this step were again 0.08 ml/min for the reaction mixture from the extraction, 0.06 ml/min for the aqueous 15% NaOH solution and 125 mln/min air. The catalyst used was platinum on activated carbon, and the processing parameters were 100° C. and 22 bar.

According to HPLC analysis, the achieved reaction mixtures contained 99.51% FDCA, 0.34% HMFCA and about 0.1% unknown side products. The yield for the overall process was determined by quantitative HPLC to be 85%.

4.) NMP/NaOH/CuO—AgO/Air/22 Bar/90° C.

i) Oxidation 1—in NMP, CuO—AgO, 17 Bar and 90° C., NaOH

The same continuous lab-plant setup as for example 1 and 2 was used for this experiment. Solution A was prepared from 16.4 g of HMF and 100 g of NMP. Solution B was a 15% solution of sodium hydroxide in water.

Flow rates for solution A was 0.08 ml/min, and 0.06 ml/min for solution B; for the air flow it was 125 ml/min. Mixing was done in a t-piece mixers, and reaction took place in a trickle bed reactor. 90° C. and 22 bar were adopted to the reactor and the hold up time was 15 minutes.

The catalyst used in this experiment was CuO/AgO catalyst on alumina. This catalyst was prepared according to literature (Tian et al., 2008).

During the experiment a slow pressure rise in the system due to plugging with insoluble humic matter is observed, leading also to reduced conversion after six hours plant operation time.

The oxidation product mixture contains according to HPLC analysis FDCA: 27.65%, HMFCA: 71.37%. No HPLC detectable amounts of FFCA, DFF or HMF were found.

ii.) Extraction with Ethyl Acetate 20.9 ml of the reaction mixture were contacted six time with 20 ml ethyl acetate each to extract NMP from the water phase.

HPLC analysis shows that FDCA and HMFCA remained completely in the water phase.

iii.) Oxidation 2—in $H_2O$, Pt—C, 17 Bar and 80° C., NaOH

The second oxidation step was done in a similar setup as in the first oxidation step and with the same parameters. Changed was only the catalyst in the reactor back to platinum on activated carbon.

The achieve reaction mixture contained 93.65% FDCA, 5.26% HMFCA and about 1% unidentified side products or intermediates. The yield of the overall oxidation process was determined by HPLC to be 88%. However, this yield could not be established for longer process times because of the plugging observed in the first oxidation step due to black tar formation.

5.) Extraction Trials i) NMP Extraction from Water Phase with Different Solvents A mixture of 24.12 g NMP (53% (w/w), hatched bar in FIG. 2) and 21.2 g deionized water were prepared as starting solution for separating NMP from water.

This solution was transferred into a separating funnel. 21.2 g of ethylacetate were added to the NMP solution, both phases were intensively contacted and then separated. The mass of the single phases were recorded and a small sample was taken from the water phase to determine NMP content by quantitative HPLC chromatography.

This procedure was repeated five times for the water phase with the same amount of fresh solvent in each step to achieve an overall of six discrete extraction steps. The remaining NMP content in the water phase was determined by quantitative HPLC chromatography.

The NMP extraction as described above for ethyl acetate was carried out with identical ratios also with dibutyl ether, toluene, tetrahyfrofuran, trichloromethane and n-butanol.

With ethyl acetate (data set 1 in FIG. 2), a remaining NMP concentration of 5.7% (dotted bar in FIG. 2) was reached. This corresponds to a removal of 89.8% of the NMP from the water phase in six extraction steps (horizontal line bar in FIG. 2). This result was beaten by trichloromethane (data set 4), which removed NMP from the water phase to an extent that it was not detectable anymore. Dibutyl ether (data set 2, 11.5%) and toluene (data set 3, 21.9%) showed significantly worse results. Tetrahydrofuran (data set 5) and n-butanol (data set 6) ended up with a one phase system.

Figure 2:
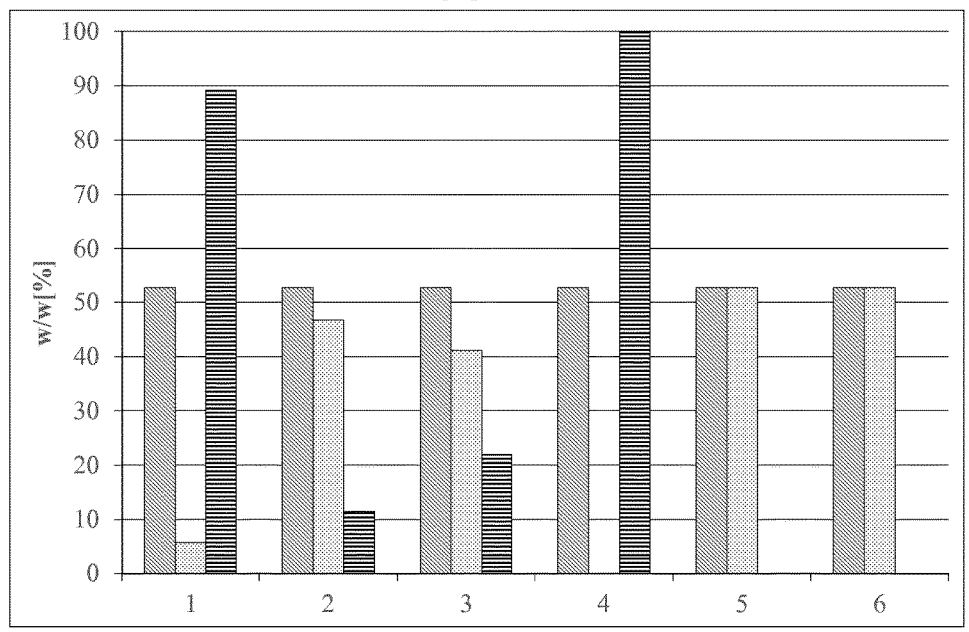
FIG. 2 shows the result of extraction trials regarding the extraction of NMP.

The result is summarized in FIG. 2. The hatched bar in this figure corresponds to the NMP starting concentration, the dotted bar to the NMP concentration after six extraction steps and the horizontal line bar to the relative amount of NMP removed in the six steps.

ii) DMSO Extraction from Water Phase with Different Solvents 17.28 g DMSO and 15.13 g deionized water were mixed and transferred into a separation funnel. 15.20 g ethyl acetate were added to this solution. The two-phase system was intensely mixed for ten minutes and then the phases separated.

The masses of both phases were recorded and a sample from the water phase was taken to be analysed in quantitative HPLC.

Extraction of NMP from the waterphase was repeated five times with 15.2 g of ethyl acetate in each step. After each single step masses were recorded and quantitative HPLC measurements were done.

The same extraction procedure as described for ethyl acetate was carried out also with dibutyl ether, toluene, trichloromethane, tetrahydrofuran and n-butanol.

Figure 3:
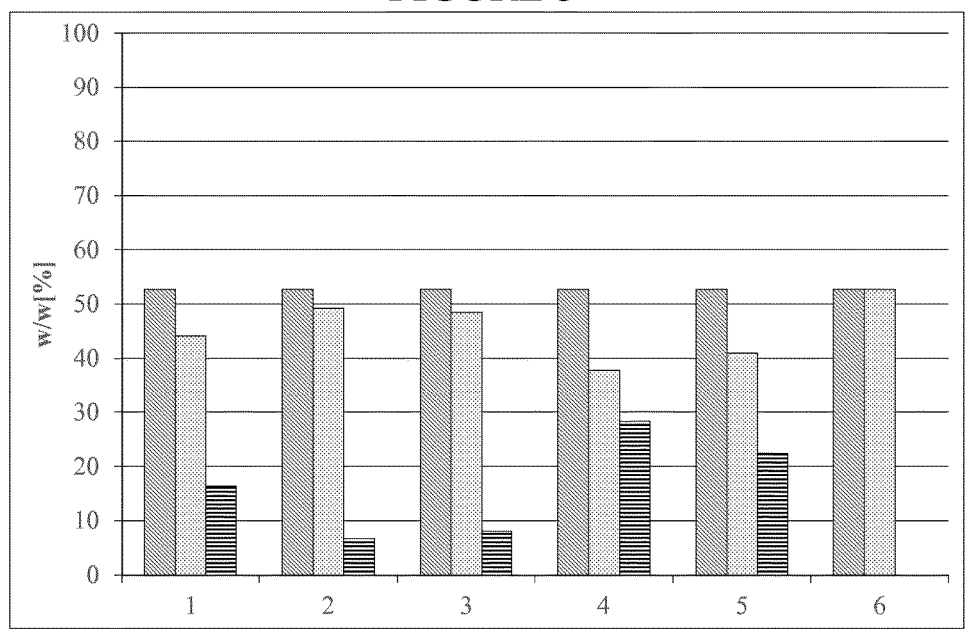
FIG. 3 shows the result of extraction trials regarding the extraction of DMSO.

The results are summarized in FIG. 3. Assignment of bars is identical to FIG. 2 described above.

16.4% of the DMSO was removed from the water phase with ethyl acetate (data set 1 in FIG. 3). Better results were achieved with trichloromethane (data set 4, 28.3%) and tetrahydrofuran (data set 5, 22.5%). Toluene (data set 3, 8.1%) and dibutylether (data set 2, 6.7%) showed an even lower DMSO removal capability. N-butanol (data set 6) did show no phase separation.

NON-PATENT LITERATURE

Amarasekara, A. S., Green, D., McMillan, E., 2008. Efficient oxidation of 5-hydroxymethylfurfural to 2, 5-diformylfuran using Mn (III)—salen catalysts. Catalysis Communications 9, 286-288.

Bicker, M., Kaiser, D., Ott, L., Vogel, H., 2005. Dehydration of D-fructose to hydroxymethylfurfural in sub- and supercritical fluids. The journal of supercritical fluids 36, 118-126.

Chheda, J. N., Roman-Leshkov, Y., Dumesic, J. A., 2007. Production of 5-hydroxymethylfurfural and furfural by dehydration of biomass-derived mono- and poly-saccharides. Green Chemistry 9, 342-350.

Grasset, F. L., Katryniok, B., Paul, S., Nardello-Rataj, V., Pera-Titus, M., Clacens, J.-M., De Campo, F., Dumeignil, F., 2013. Selective oxidation of 5-hydroxymethylfurfural to 2, 5-diformylfuran over intercalated vanadium phosphate oxides. RSC Advances 3, 9942-9948.

Lewkowski, J., 2001. Synthesis, chemistry and applications of 5-hydroxymethyl-furfural and its derivatives. Arkivoc I, 17-54.

Teong, S. P., Yi, G., Zhang, Y., 2014. Hydroxymethylfurfural production from bioresources: past, present and future. Green Chemistry 16, 2015-2026.

Tian, Q., Shi, D., Sha, Y., 2008. CuO and Ag2O/CuO catalyzed oxidation of aldehydes to the corresponding carboxylic acids by molecular oxygen. Molecules 13, 948-957.

Tuercke, T., Panic, S., Loebbecke, S., 2009. Microreactor Process for the Optimized Synthesis of 5-Hydroxymethylfurfural: A Promising Building Block Obtained by Catalytic Dehydration of Fructose. Chemical engineering & technology 32, 1815-1822.

The invention claimed is:

1. A process for the production of 2,5-furandicarboxylic acid (FDCA) via oxidation of 5-hydroxymethyl-2-furfural (HMF), said HMF being present in a solution in a high-boiling polar solvent and water, the process comprising:
   in a first oxidation step, at least partially oxidizing the HMF in said solution to yield a first reaction mixture comprising at least one monoacid selected from the group consisting of 5-hydroxymethylfuran-2-carboxylic acid (HMFA) and 5-formylfuran-2-carboxylic acid (FFCA) and, optionally, FDCA,
   in an extraction step after the first oxidation step, extracting said high-boiling polar solvent from said first reaction mixture by means of an extraction solvent, wherein said at least one monoacid remains in an aqueous phase, and
   in a second oxidation step oxidizing said at least one monoacid to FDCA,
   wherein the high-boiling polar solvent is selected from the group consisting of Dimethylsulfoxide (DMSO), N-Methyl-2-pyrrolidone (NMP), N,N-Dimethylformamide (DMF), N,N-Dimethylacetamide (DMA), and mixtures thereof,
   wherein, in the first oxidation step, a base with a pKa value of from 7.5 to 13.0 is employed, and
   wherein the water content of said solution before the first oxidation step is from 1% to 80%.

2. A process according to claim 1, wherein the high-boiling polar solvent is selected from the group consisting of polar aprotic solvents and mixtures thereof.

3. A process according to claim 1, wherein the extraction solvent for the extraction step is selected from the group consisting of ethylacetate, trichlorom ethane, and mixtures thereof.

4. A process according to claim 1, wherein the oxidizing agent for said first oxidation step or said second oxidation step or for both oxidation steps is selected from oxygen or air.

5. A process according to claim 1, wherein, in said first oxidation step, parts of the HMF remain unreacted and/or are oxidized to 2,5-diformylfuran (DFF), and wherein, in said extraction step, said unreacted HMF and/or said DFF are extracted from said first reaction mixture.

6. A process according to claim 5, wherein said extracted unreacted HMF and/or said extracted DFF are recycled to the solution before the first oxidation step.

7. A process according to claim 1, wherein, after the extraction step, the extraction solvent and the high boiling polar solvent are separated from each other.

8. A process according to claim 1, wherein the base is selected from the group consisting of phosphates, carbonates, and mixtures thereof.

9. A process according to claim 8, wherein the base is selected from the group consisting of $Na_3PO_4$, $Na_2HPO_4$, and mixtures thereof.

10. A process according to claim 1, wherein the water content of said solution before the first oxidation step is from 30% to 50%.

11. A process according to claim 1, wherein, in the second oxidation step, a base with a pKa value of above 13.0 is employed.

12. A process according to claim 1, wherein the base employed in the second oxidation step is NaOH.

\* \* \* \* \*

UNITED STATES PATENT AND TRADEMARK OFFICE
CERTIFICATE OF CORRECTION

PATENT NO. : 10,316,011 B2  
APPLICATION NO. : 16/060382  
DATED : June 11, 2019  
INVENTOR(S) : Tekautz et al.

Page 1 of 1

It is certified that error appears in the above-identified patent and that said Letters Patent is hereby corrected as shown below:

In the Specification

<u>Column 4</u>
Line 8, change "to oxidize" to –the oxidation of–

<u>Column 9</u>
Line 67, change "mixers" to –mixer–

<u>Column 10</u>
Line 17, change "time" to –times–
Line 30, change "achieve" to –achieved–

Signed and Sealed this
Eighth Day of October, 2019

Andrei Iancu
*Director of the United States Patent and Trademark Office*